US00PP11707P

United States Patent [19]

Zary

[11] Patent Number: Plant 11,707

[45] Date of Patent: Dec. 19, 2000

[54] FLORIBUNDA ROSE PLANT NAMED 'JACCHAMP'

[75] Inventor: Keith W. Zary, Thousand Oaks, Calif.

[73] Assignee: Bear Creek Gardens, Inc., Medford, Oreg.

[21] Appl. No.: 09/234,793

[22] Filed: Jan. 20, 1999

[51] Int. Cl.[7] ..... A01H 5/00

[52] U.S. Cl. ..... Plt./144

[58] Field of Search ..... Plt./133, 134, 144, Plt./145

[56] References Cited

PUBLICATIONS

UPOV–ROM, Feb. 1999, Plant Variety Database, G.TI Jouve Retrieval Software, citation for 'JACchamp'.

*Primary Examiner*—Howard J. Locker

*Attorney, Agent, or Firm*—Klarquist Sparkman Campbell Leigh & Whinston, LLP

[57] ABSTRACT

Floribunda rose plant having strong, upright growth, high production of well formed, thick petaled, medium-sized flowers, on medium length stems, and long vase life.

1 Drawing Sheet

The present invention relates to a new and distinct variety of rose plant of the floribunda class which was originated by me by crossing the variety 'KORokis', (unpatented), with the variety 'KORampa', U.S. Plant Pat. No. 5411.

The primary objective of this breeding was to produce a new rose variety having thick petals, medium length stems, strong vertical growth, high production of medium-sized flowers, and a long vase life. The objective was substantially achieved, along with other desirable improvements, as evidenced by the following unique combination of characteristics that are outstanding in the new variety and that distinguish it from its parents, as well as from all other varieties of which I am aware:

1. High cut flower production;
2. Long vase life;
3. Well-formed, medium-sized flowers;
4. Stems 18–22 inches;
5. Strong, upright growth; and
6. Moderate flower fragrance.

'JACchamp' is a greenhouse cut rose variety. It produces medium length stems (18–22 inches). Its growth is vigorous and upright. 'JACchamp' will produce 260–280 stems per $m^2$ of greenhouse. Flowers have very good vase life (14–16 days).

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent*.—'KORokis' (unpatented).

*Pollen parent*.—'KORampa' (U.S. Plant Pat. No. 5411)

Classification:

*Botanical*.—*Rosa hybrida*.

*Commercial*.—Floribunda.

FLOWER

Observations made from specimens grown in a greenhouse environment at Somis, Calif., February 1996 to December 1998.

Blooming habit: Continuous.

Bud:

*Size*.—One and one-half inches long when the petals start to unfurl.

*Form*.—The bud form is long, pointed ovoid.

*Color*.—When sepals first divide, bud color is Yellow-White Group 158D at the petal tips. Near the base, the color is close to Yellow Group 11D. The middle portion of the bud is Yellow White Group 158D. When half blown, the upper and lower sides of the petals are Yellow-White Group 158D on the outer two-thirds of the petals. The inner one-third's are Yellow Group 11D.

*Sepals*.—Color: Green Group 137D. Surface texture: Covered in fine hairs. There are three normally to heavily appendaged sepals. There are two unappendaged sepals with smooth edges.

*Receptacle*.—Color: Yellow-Green Group 146C. Shape: Funnel. Size: Small, about 5/16"×5/16". Surface: Smooth.

*Peduncle*.—Length: Medium, averaging about three inches. Surface: Smooth. Color: Yellow-Green Group 146C. Strength: Stiff, erect.

Bloom:

*Size*.—Medium. Average open size is four inches.

*Borne*.—Singly and occasionally several together in pyramidal clusters of three to five blooms.

*Stems*.—Strength: Strong. Average length is about eighteen to twenty-two inches.

*Form*.—When first open: High-centered. Permanence:. Retains its form to the end, outer petals curl back with some quilling.

*Petalage*.—Number of petals under normal conditions: 30–35.

*Color*.—The upper and lower sides of the petals are Yellow-White Group 158D on the outer two-thirds of a petal, the inner one-third of a petal is Yellow Group 11D. The base of each petal has a small (3/16"×3/16"), Yellow Group 3C spot on the upper surface at the point of attachment. On the lower surface, the spot is Yellow Group 4C. The major color on the upper side is Yellow-White Group 158D.

*Variegations*.—None.

*Discoloration*.—The general tonality at the end of the first day: No change. At the end of the third day: No change. No change through to petal drop in the vase. On the plant, the color by day six or seven, will fade to White Group 155D followed on day eight or nine by petal drop.

*Fragrance*.—Moderate, anise.

Petals:

*Texture*.—Thick.

*Shape*.—Round.

*Form*.—Tips slightly recurved, edges slightly quilled.

*Arrangement*.—Imbricated. Petaloids in the center: None.

*Persistence*.—Petals drop off cleanly before drying.

*Lastingness*.—On the plant: Long (eight to nine days). As a cut flower: Long (about fourteen to fifteen days).

Reproductive parts:

*Anthers*.—Size: Medium. Quantity: Many. Color: Yellow Group 11B. Arrangement: Regular around styles.

*Filaments*.—Color: Yellow Group 11C with some pink near the bottom of the filaments.

*Pollen*.—Color: Present.

*Styles*.—Color: Green-Yellow Group 1D.

*Stigmas*.—Color: Yellow-White Group 158A.

Plant:

*Form*.—Bush.

*Growth*.—Vigorous, upright, branching. Mature plant height is about five feet, width is about three and one-half feet.

Foliage: Number of leaflets on normal mid-stem leaves: Five.

*Size*.—Medium to large (6" long×4½" wide).

*Quantity*.—Abundant.

*Color*.—New foliage: Upper and lower surfaces: Greyed-Red Group 178A. The upper surface rapidly becomes green. The lower surface takes several days to green. Old foliage: Upper surface: Green Group 139A. Lower surface: Green Group 139C.

Leaflets:

*Shape*.—Pointed oval.

*Texture*.—Leathery, glossy.

*Edge*.—Smooth, serrated.

*Serration*.—Single.

*Petiole rachis*.—Greyed-Purple Group 183A.

*Petiole underside*.—Smooth with an occasional prickle.

*Stipules*.—Medium (½"), serrated, bearded.

*Disease resistance*.—Resistant to mildew under normal growing conditions in a greenhouse. Not tested for rust or blackspot.

Wood:

*New wood*.—Color: Yellow-Green Group 146C. Bark: Smooth.

*Old wood*.—Color: Green Group 137C. Bark: Smooth.

Prickles:

*Quantity*.—On main canes from base: Ordinary. On laterals from main canes: Ordinary.

*Form*.—Medium, hooked downward.

*Color when young*.—Greyed-Purple Group 183B.

*Color when mature*.—Greyed-Orange Group 168D.

Small prickles:

*Quantity*.—On main stalks: None. On laterals: None.

I claim:

1. A new and distinct variety of rose plant of the floribunda class, substantially as herein shown and described, characterized particularly by its strong, upright growth, high production of well formed, thick petaled, medium-sized flowers, on medium length stems, and long vase life.

* * * * *

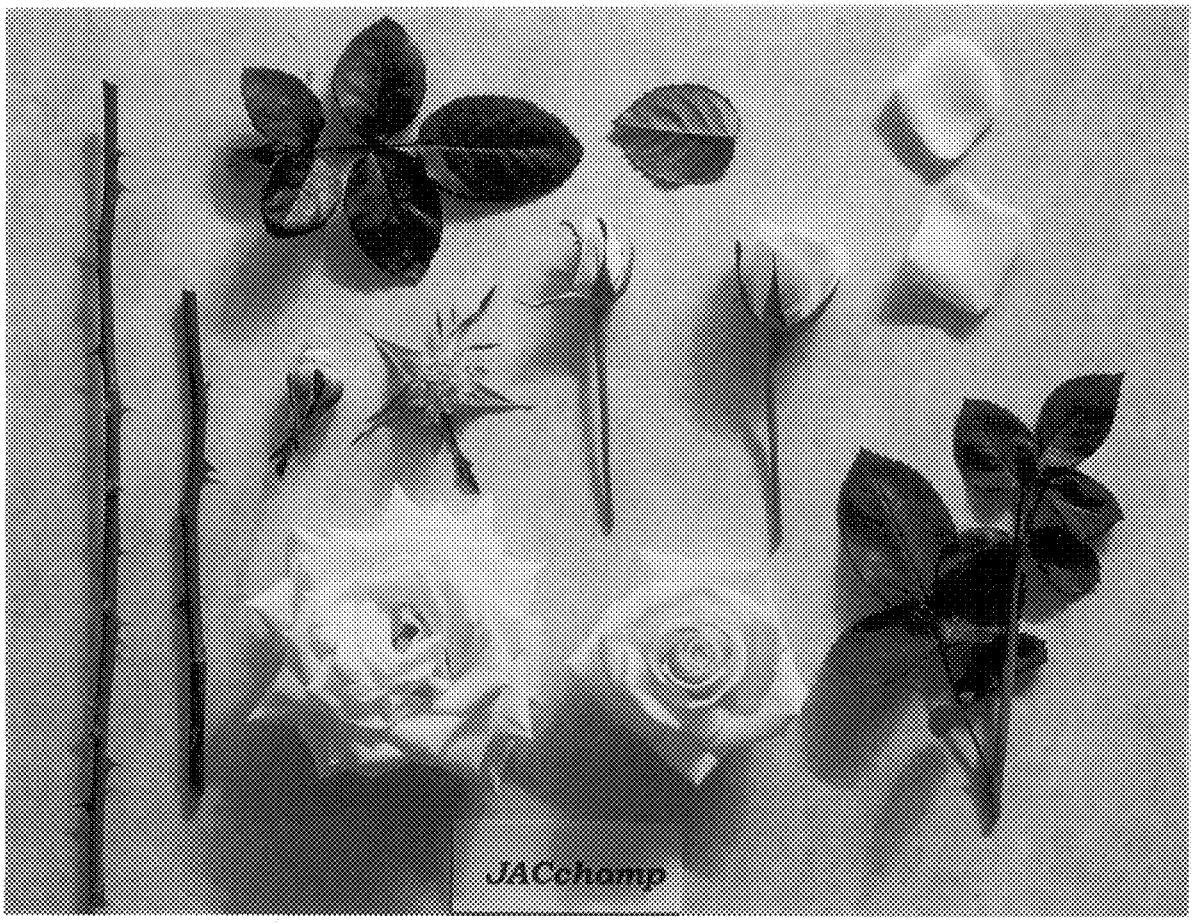
JACchamp